(12) United States Patent
Tsymbalenko et al.

(10) Patent No.: US 11,602,332 B2
(45) Date of Patent: Mar. 14, 2023

(54) METHODS AND SYSTEMS FOR MULTI-MODE ULTRASOUND IMAGING

(71) Applicant: GE Precision Healthcare LLC, Milwaukee, WI (US)

(72) Inventors: Yelena Viktorovna Tsymbalenko, Mequon, WI (US); Michael Washburn, Brookfield, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 140 days.

(21) Appl. No.: 16/667,747

(22) Filed: Oct. 29, 2019

(65) Prior Publication Data

US 2021/0121158 A1 Apr. 29, 2021

(51) Int. Cl.
| | | |
|---|---|---|
| *A61B 8/00* | (2006.01) | |
| *A61B 8/08* | (2006.01) | |
| *A61B 5/00* | (2006.01) | |

(52) U.S. Cl.
CPC .............. *A61B 8/54* (2013.01); *A61B 5/4887* (2013.01); *A61B 5/7264* (2013.01); *A61B 8/4254* (2013.01); *A61B 8/469* (2013.01); *A61B 8/488* (2013.01); *A61B 8/5223* (2013.01); *A61B 8/58* (2013.01)

(58) Field of Classification Search
CPC ....... A61B 8/54; A61B 5/7264; A61B 8/4254; A61B 8/469; A61B 8/488; A61B 8/5223; A61B 8/58; A61B 5/4887–4896
See application file for complete search history.

(56) References Cited

U.S. PATENT DOCUMENTS

| | | | | |
|---|---|---|---|---|
| 5,315,999 | A * | 5/1994 | Kinicki .................. | A61B 8/467 600/443 |
| 7,648,460 | B2 * | 1/2010 | Simopoulos ........... | G16H 30/20 600/437 |
| 7,846,098 | B2 * | 12/2010 | Bakircioglu ............. | A61B 8/06 600/440 |
| 7,903,852 | B2 * | 3/2011 | Springorum .............. | G06T 7/80 382/128 |
| 8,235,900 | B2 * | 8/2012 | Hao ..................... | A61B 8/0825 600/437 |
| 8,235,905 | B2 * | 8/2012 | Lin ........................ | G01S 7/5205 600/443 |
| 8,715,187 | B2 | 5/2014 | Landberg Davis et al. | |
| 9,848,849 | B2 * | 12/2017 | Pfeiffer .................... | A61B 8/13 |
| 9,855,020 | B2 * | 1/2018 | Nair ......................... | A61B 8/54 |
| 10,154,826 | B2 | 12/2018 | Singh et al. | |
| 10,194,888 | B2 * | 2/2019 | Henderson ............. | A61B 8/469 |

(Continued)

*Primary Examiner* — Joel Lamprecht
*Assistant Examiner* — Nyrobi Celestine
(74) *Attorney, Agent, or Firm* — McCoy Russell LLP

(57) ABSTRACT

Various methods and systems are provided for automatically or semi-automatically adjusting one or more ultrasound imaging parameters for imaging in a second mode based on images obtained in a first mode. In one example, a method includes operating an ultrasound imaging system in a first operating mode, determining an anatomy imaged by the ultrasound imaging system in the first operating mode, and responsive to an operating mode transition request, adjusting imaging parameters of the ultrasound imaging system in a second operating mode based on the first operating mode and the anatomy imaged in the first operating mode.

18 Claims, 4 Drawing Sheets
(2 of 4 Drawing Sheet(s) Filed in Color)

(56) References Cited

U.S. PATENT DOCUMENTS

| | | | |
|---|---|---|---|
| 2004/0102706 A1* | 5/2004 | Christopher | G01S 7/52071 600/453 |
| 2005/0049506 A1* | 3/2005 | Jackson | G01S 7/52098 600/455 |
| 2005/0131300 A1* | 6/2005 | Bakircioglu | A61B 8/06 600/453 |
| 2008/0130972 A1* | 6/2008 | Miller | G06T 7/20 705/3 |
| 2009/0012393 A1* | 1/2009 | Choi | A61B 8/463 600/437 |
| 2010/0004539 A1* | 1/2010 | Chen | A61B 8/462 600/445 |
| 2010/0240994 A1* | 9/2010 | Zheng | A61B 8/00 600/440 |
| 2012/0092527 A1* | 4/2012 | Lavin | A61B 8/467 348/E5.051 |
| 2013/0144168 A1* | 6/2013 | Yoneyama | A61B 8/4477 600/443 |
| 2015/0272547 A1* | 10/2015 | Freiburger | A61B 8/52 600/438 |
| 2015/0351726 A1* | 12/2015 | Menon | A61B 8/08 600/443 |
| 2016/0143629 A1* | 5/2016 | Buckton | A61B 8/543 600/440 |
| 2017/0143312 A1* | 5/2017 | Hedlund | G01S 7/5205 |
| 2017/0238909 A1* | 8/2017 | Shin | A61B 5/1075 |
| 2018/0055479 A1* | 3/2018 | Lalena | A61B 8/4461 |
| 2018/0064403 A1* | 3/2018 | Konta | A61B 5/055 |
| 2018/0070924 A1* | 3/2018 | Kawabata | A61B 8/5238 |
| 2018/0116633 A1* | 5/2018 | Hansen | A61B 8/467 |
| 2019/0269384 A1* | 9/2019 | Lundberg | G06N 3/08 |
| 2019/0380676 A1* | 12/2019 | Swan | G16H 20/40 |
| 2020/0214676 A1* | 7/2020 | McLaughlin | G06T 5/001 |
| 2020/0364515 A1* | 11/2020 | Heide | G06T 5/001 |
| 2021/0052255 A1 | 2/2021 | Cadieu et al. | |
| 2021/0059644 A1* | 3/2021 | Liu | A61B 8/465 |
| 2021/0093301 A1* | 4/2021 | Wang | G06K 9/00221 |
| 2021/0373154 A1* | 12/2021 | Wang | A61B 8/488 |

\* cited by examiner

METHODS AND SYSTEMS FOR MULTI-MODE ULTRASOUND IMAGING

FIELD

Embodiments of the subject matter disclosed herein relate to ultrasound imaging.

BACKGROUND

A medical diagnostic ultrasound imaging system typically includes a set of selectable imaging modes, such as a B-mode and color flow Doppler mode. The ultrasound imaging system may operate in the selected imaging mode and may be adjusted to operate in a different imaging mode according to user preference. For B-mode imaging, the ultrasound imaging system generates a two-dimensional image of tissue in which the brightness of a pixel corresponds to the intensity of the echo return. Alternatively, in a color flow imaging mode, the Doppler effect is used to detect the presence of blood flow in the body. Flow velocities in a given location in a vessel can be estimated using the measured Doppler shift and correcting for the Doppler angle between the ultrasound beams and the vessel orientation.

BRIEF DESCRIPTION

In one embodiment, a method includes operating an ultrasound imaging system in a first operating mode, determining an anatomy imaged by the ultrasound imaging system in the first operating mode, and responsive to an operating mode transition request, adjusting imaging parameters of the ultrasound imaging system in a second operating mode based on the first operating mode and the anatomy imaged in the first operating mode It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure will be better understood from reading the following description of non-limiting embodiments, with reference to the attached drawings, wherein below.

DETAILED DESCRIPTION

Figure 1:
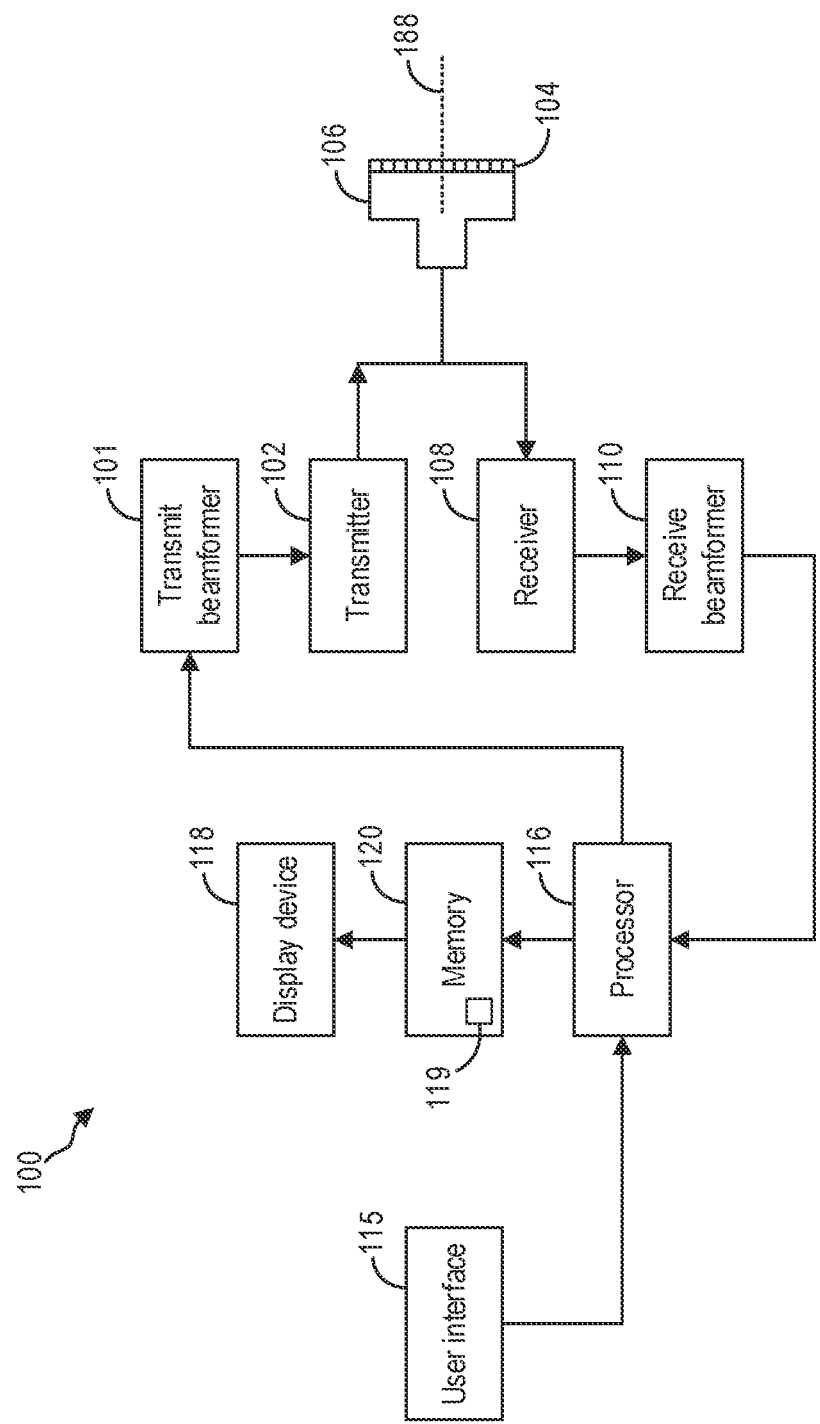
FIG. 1 shows an example ultrasound imaging system according to an embodiment.

The following description relates to various embodiments of ultrasound imaging using an ultrasound imaging system, such as the ultrasound imaging system shown in FIG. 1. The ultrasound imaging system is configured to operate in at least a first imaging mode and a second imaging mode, such as a B-mode and a color flow Doppler mode. The ultrasound imaging system may transition between the two modes in response to input by an operator of the ultrasound imaging system, such as a clinician. Following a request to transition from the first mode to the second mode, the ultrasound imaging system generates recommended imaging parameters for operating in the second imaging mode based on images acquired while operating in the first imaging mode, as illustrated by the flow chart of FIG. 2. The recommended imaging parameters may be generated according to an algorithm stored in a memory of the ultrasound imaging system and may be based on an anatomy being imaged.

Figure 3:
FIG. 3 shows an ultrasound image of a first anatomical structure acquired in a first imaging mode.
Figure 4:
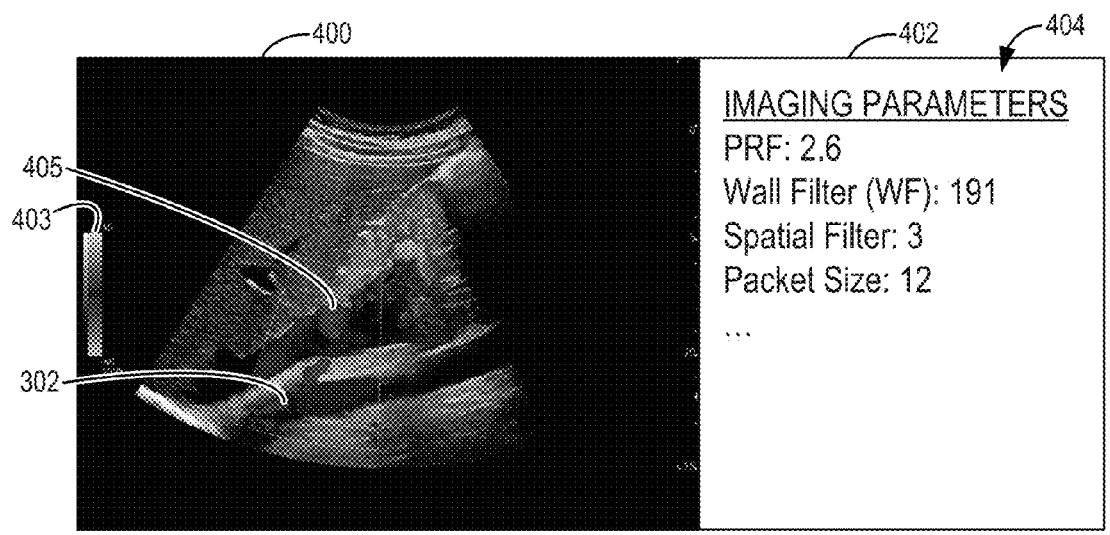
FIG. 4 shows an ultrasound image of the first anatomical structure of FIG. 3 acquired in a second imaging mode, without assisted selection of ultrasound imaging parameters.
Figure 5:
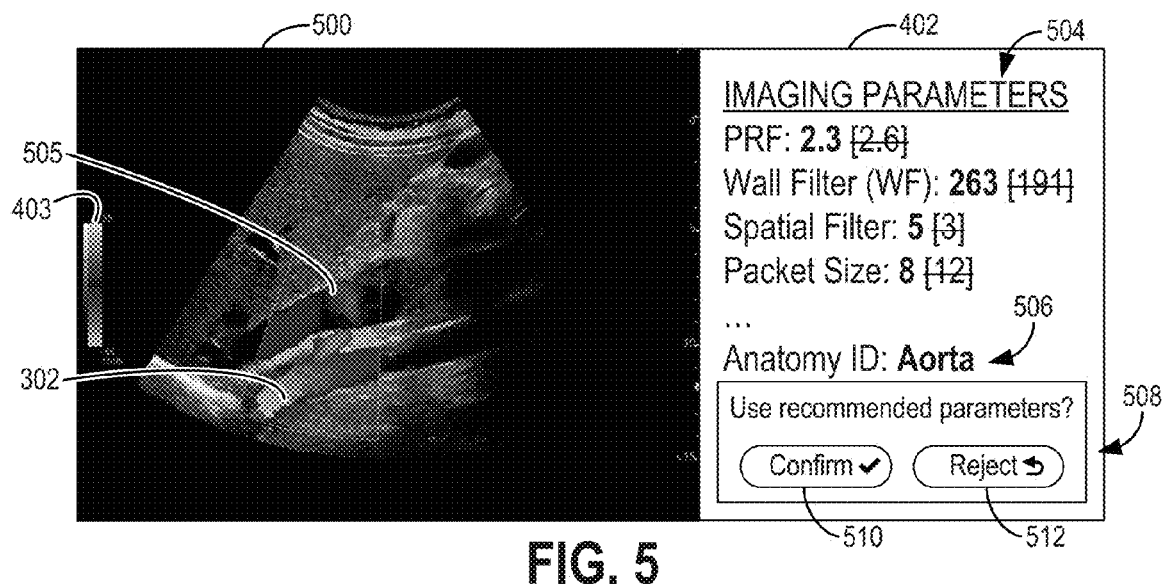
FIG. 5 shows an ultrasound image of the first anatomical structure of FIGS. 3-4 acquired in the second imaging mode, with assisted selection of ultrasound imaging parameters.
Figure 6:
FIG. 6 shows an ultrasound image of a second anatomical structure acquired in the first imaging mode.
Figure 7:
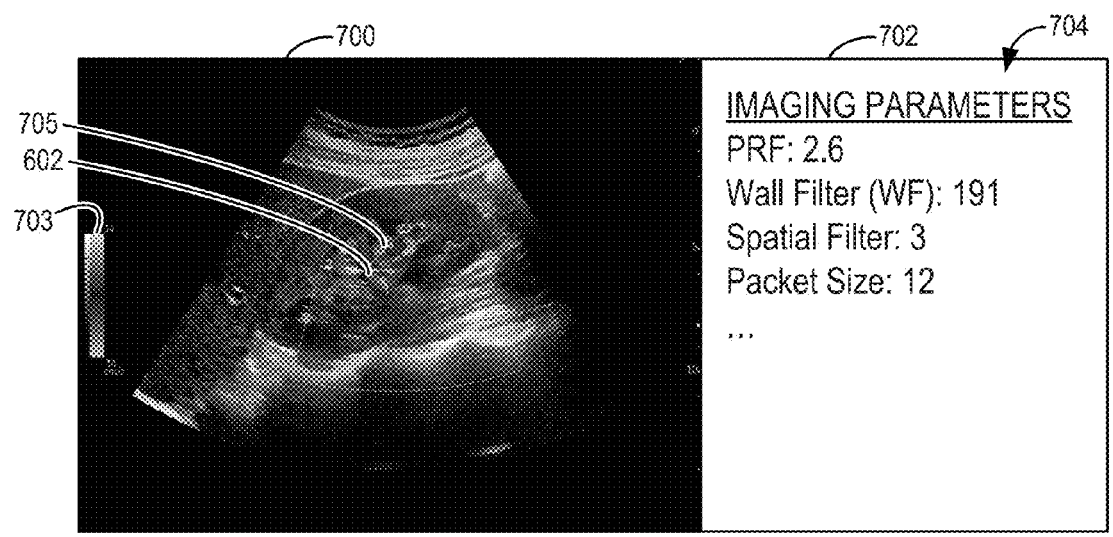
FIG. 7 shows an ultrasound image of the second anatomical structure of FIG. 6 acquired in the second imaging mode, without assisted selection of ultrasound imaging parameters.
Figure 8:
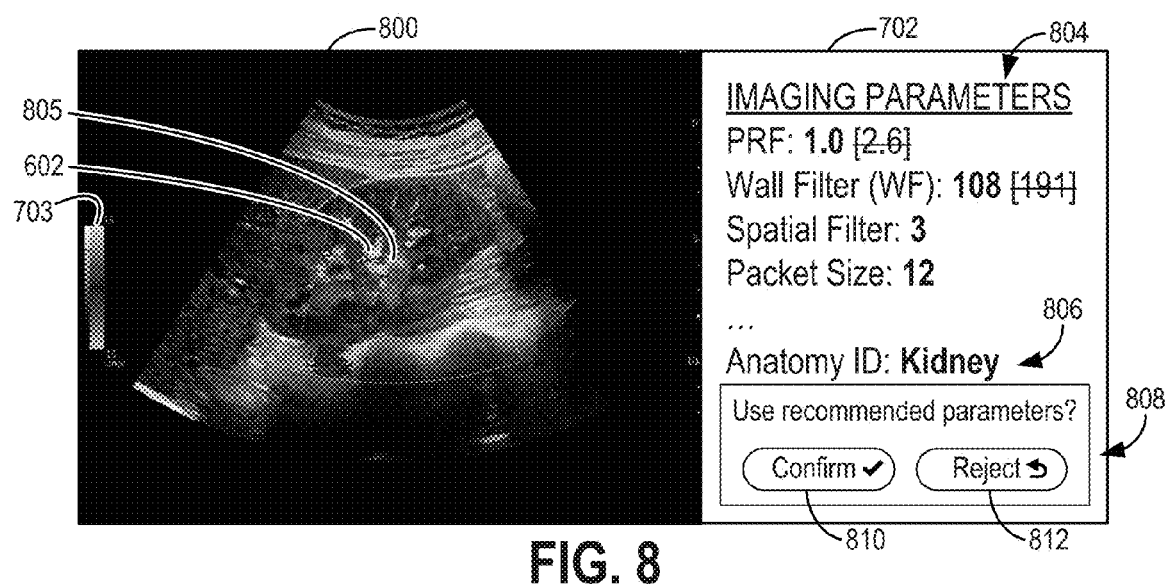
FIG. 8 shows an ultrasound image of the second anatomical structure of FIGS. 6-7 acquired in the second imaging mode, with assisted selection of ultrasound imaging parameters.

For example, while imaging a first anatomical structure in the first mode as shown by FIG. 3, the operator may transition the ultrasound imaging system to imaging in the second mode, and the ultrasound imaging system may provide recommended imaging parameters (e.g., imaging parameter values) for imaging the same structure in the second imaging mode, as shown by FIG. 5. The operator may accept the recommended imaging parameters, or the operator may reject the recommended imaging parameters in order to proceed with imaging in the second mode without the recommended imaging parameters, as shown by FIG. 4. When imaging a different, second anatomical structure in the first mode, as shown by FIG. 6, transitioning the ultrasound imaging system to the second mode may provide different recommended imaging parameters relative to conditions in which the first anatomical structure is imaged, as shown by FIG. 8. The operator may optionally reject the recommended imaging parameters and proceed with imaging in the second mode without the recommended imaging parameters, as shown by FIG. 7.

By providing the recommended imaging parameters when transitioning between imaging modes, an image quality of the ultrasound imaging system may be increased. For example, providing the recommended imaging parameters based on the anatomical structure being imaged may increase a clarity of various features of the anatomical structure in the images generated by the ultrasound imaging system. Further, by providing the recommended imaging parameters when transitioning between imaging modes, the operator may more easily select imaging parameters that will increase the image clarity without adjusting each imaging parameter individually. As a result, a cognitive load on the operator may be reduced, and an amount of time to image the subject may be decreased.

Referring now to FIG. 1, a schematic diagram of an ultrasound imaging system 100 is shown in accordance with an embodiment. The ultrasound imaging system 100 includes a transmit beamformer 101 and a transmitter 102 that drive elements 104 within a transducer array of ultrasound probe 106 to emit pulsed ultrasonic signals into a body of a subject (e.g., a patient, not shown). The ultrasound probe 106 may, for instance, comprise a linear array probe, a curvilinear array probe, a sector probe, or any other type of ultrasound probe configured to acquire both two-dimensional (2D) B-mode data and 2D color flow data or both 2D B-mode data and another ultrasound mode that detects blood flow velocity in the direction of a vessel axis. The elements 104 of the ultrasound probe 106 may therefore be arranged in a one-dimensional (1D) or 2D array. The pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the ultrasound probe 106. The terms "scan" or "scanning" may also be used in this disclosure to refer to acquiring data through the process of transmitting and receiving ultrasonic signals. The term "data" and "ultrasound data" may be used in this disclosure to refer to one or more datasets acquired with an ultrasound imaging system.

A user interface 115 may be used to control operation of the ultrasound imaging system 100, including, to control the input of patient data, to change a scanning or display parameter, to select various modes, operations, and parameters, and the like. The user interface 115 may include one or more of a rotary, a mouse, a keyboard, a trackball, hard keys linked to specific actions, soft keys that may be configured to control different functions, a graphical user interface displayed on the display device 118 in embodiments wherein display device 118 comprises a touch-sensitive display device or touch screen, and the like. In some examples, the user interface 115 may include a proximity sensor configured to detect objects or gestures that are within several centimeters of the proximity sensor. The proximity sensor may be located on either the display device 118 or as part of a touch screen. The user interface 115 may include a touch screen positioned in front of the display device 118, for example, or the touch screen may be separate from the display device 118.

Physical controls of the user interface 115 such as buttons, sliders, rotary knobs, keyboards, mice, trackballs, and so on, may be included alone or in combination with graphical user interface icons displayed on the display device 118. The display device 118 may be configured to display a graphical user interface (GUI) from instructions stored in memory 120. The GUI may include user interface icons to represent commands and instructions. The user interface icons of the GUI are configured so that a user may select commands associated with each specific user interface icon in order to initiate various functions controlled by the GUI. For example, various user interface icons may be used to represent windows, menus, buttons, cursors, scroll bars, and so on. According to embodiments where the user interface 115 includes a touch screen, the touch screen may be configured to interact with the GUI displayed on the display device 118. The touch screen may be a single-touch touch screen that is configured to detect a single contact point at a time or the touch screen may be a multi-touch touch screen that is configured to detect multiple points of contact at a time. For embodiments where the touch screen is a multi-point touch screen, the touch screen may be configured to detect multi-touch gestures involving contact from two or more of a user's fingers at a time. The touch screen may be a resistive touch screen, a capacitive touch screen, or any other type of touch screen that is configured to receive inputs from a stylus or one or more of a user's fingers. According to other embodiments, the touch screen may comprise an optical touch screen that uses technology such as infrared light or other frequencies of light to detect one or more points of contact initiated by a user.

According to various embodiments, the user interface 115 may include an off-the-shelf consumer electronic device such as a smartphone, a tablet, a laptop, and so on. For the purposes of this disclosure, the term "off-the-shelf consumer electronic device" is defined to be an electronic device that was designed and developed for general consumer use and one that was not specifically designed for use in a medical environment. According to some embodiments, the consumer electronic device may be physically separate from the rest of the ultrasound imaging system 100. The consumer electronic device may communicate with the processor 116 through a wireless protocol, such as Wi-Fi, Bluetooth, Wireless Local Area Network (WLAN), near-field communication, and so on. According to an embodiment, the consumer electronic device may communicate with the processor 116 through an open Application Programming Interface (API).

The ultrasound imaging system 100 also includes a processor 116 to control the transmit beamformer 101, the transmitter 102, the receiver 108, and the receive beamformer 110. The processor 116 is configured to receive inputs from the user interface 115. The receive beamformer 110 may comprise either a conventional hardware beamformer or a software beamformer according to various embodiments. If the receive beamformer 110 is a software beamformer, the receive beamformer 110 may comprise one or more of a graphics processing unit (GPU), a microprocessor, a central processing unit (CPU), a digital signal processor (DSP), or any other type of processor capable of performing logical operations. The receive beamformer 110 may be configured to perform conventional beamforming techniques as well as techniques such as retrospective transmit beamforming (RTB). If the receive beamformer 110 is a software beamformer, the processor 116 may be configured to perform some or all of the functions associated with the receive beamformer 110.

The processer 116 is in electronic communication with the ultrasound probe 106. For purposes of this disclosure, the term "electronic communication" may be defined to include both wired and wireless communications. The processor 116 may control the ultrasound probe 106 to acquire data. The processor 116 controls which of the elements 104 are active and the shape of a beam emitted from the ultrasound probe 106. The processor 116 is also in electronic communication with a display device 118, and the processor 116 may process the data into images for display on the display device 118. The processor 116 may include a CPU according to an embodiment. According to other embodiments, the processor 116 may include other electronic components capable of carrying out processing functions, such as a GPU, a microprocessor, a DSP, a field-programmable gate array (FPGA), or any other type of processor capable of performing logical operations.

According to other embodiments, the processor 116 may include multiple electronic components capable of carrying out processing functions. For example, the processor 116 may include two or more electronic components selected from a list of electronic components including: a CPU, a DSP, an FPGA, and a GPU. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received.

For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. The memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, color flow Doppler mode, M-mode, Color M-mode, spectral Doppler, Elastography, TVI, strain, strain rate, and the like) to form 2D or 3D data. For example, one or more modules may generate B-mode, color flow Doppler mode, M-mode, color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

As mentioned above, the ultrasound probe 106 may comprise a linear probe or a curved array probe. FIG. 1 further depicts a longitudinal axis 188 of the ultrasound probe 106. The longitudinal axis 188 of the ultrasound probe 106 extends through and is parallel to a handle of the ultrasound probe 106. Further, the longitudinal axis 188 of the ultrasound probe 106 is perpendicular to an array face of the elements 104.

The ultrasound imaging system 100 is configured to provide recommended imaging parameters to a user (e.g., operator, such as a clinician) of the ultrasound imaging system 100 during conditions in which the user transitions operation of the ultrasound imaging system 100 between imaging modes. For example, the user may transition the ultrasound imaging system 100 from operating in a first imaging mode (e.g., the B-mode) to operating in a second imaging mode (e.g., the color flow Doppler mode). Responsive to the request input by the user to transition to the second imaging mode, the ultrasound imaging system 100 provides recommended imaging parameters for imaging in the second imaging mode, with the recommended imaging parameters being based on an anatomy imaged while in the first imaging mode.

In some examples, the ultrasound imaging system 100 may periodically track the anatomy being imaged while operating in the first imaging mode and may store the tracked anatomy in memory. As one example, at a given moment in time (referred to herein as t1) while imaging in the first imaging mode, the ultrasound imaging system may analyze a pre-determined number of images (e.g., five images) stored in memory that were acquired sequentially by the ultrasound imaging system immediately prior to the time t1. The ultrasound imaging system may determine the anatomy being imaged (e.g., a kidney) at time t1 based on the images acquired prior to time t1 according to an algorithm or model (e.g., deep learning model) stored in the memory of the ultrasound imaging system, as described further below, and the determined anatomy may be stored in the memory as the anatomy currently being imaged. After some time elapses following time t1 (e.g., 5 seconds), at time t2, the ultrasound imaging system may again determine the anatomy being imaged based on images acquired sequentially immediately prior to time t2 (e.g., during the time elapsed between time t1 and time t2), and the ultrasound imaging system 100 may store the determined anatomy in memory as the anatomy currently being imaged. Responsive to the user request to transition the ultrasound imaging system 100 from imaging in the first imaging mode to imaging in the second imaging mode, the ultrasound imaging system 100 may provide recommended imaging parameters based on the most recent determined anatomy stored in memory.

As another example, the ultrasound imaging system 100 may not periodically track the anatomy being imaged and may instead determine the anatomy being imaged responsive to the user request to transition from the first imaging mode to the second imaging mode. For example, as the user inputs the request to transition from the first imaging mode to the second imaging mode, the ultrasound imaging system 100 may analyze a first pre-determined number of images (e.g., five images) acquired sequentially immediately prior to the transition request in order to determine the anatomy being imaged. The ultrasound imaging system 100 then provides the user with recommended imaging parameters for the second imaging mode based on the anatomy determined as a result of the analysis of the images acquired while imaging in the first imaging mode. In some examples, if the ultrasound imaging system 100 is unable to determine the anatomy being imaged based on the first pre-determined number of images analyzed by the ultrasound imaging system 100 responsive to the transition request (e.g., due to a high amount of noise and/or anatomical variation associated with the images), the ultrasound imaging system 100 may expand the number of images analyzed to a larger, second number of images (e.g., 10 images) acquired sequentially immediately prior to the transition request and may analyze the images to attempt to determine the anatomy being imaged. The ultrasound imaging system 100 may repeat this process in some examples, each time expanding the number of analyzed images, until the anatomy being imaged is determined.

The recommended imaging parameters provided by the ultrasound imaging system 100 responsive to a mode transition request (e.g., a user request to transition from one imaging mode to another) are based on the anatomy being imaged, as well as the mode to which the user is requesting the transition. For example, when transitioning from a first mode (e.g., B-mode) to a second mode (e.g., color flow Doppler mode), the ultrasound imaging system 100 determines the anatomy being imaged, as described above. The ultrasound imaging system 100 then provides recommended imaging parameters for imaging in the second mode based on the anatomy being imaged. However, the recommended imaging parameters provided when transitioning from the first mode to the second mode may be different than the recommended imaging parameters provided when transitioning from the second mode to the first mode. For example, during conditions in which the anatomy being imaged is a kidney (as one non-limiting example) and the user inputs a request to transition from the B-mode to the color flow Doppler mode, the ultrasound imaging system 100 may provide a first set of recommended imaging parameters (e.g., a first imaging preset), with the first set of recommended imaging parameters configured to increase the imaging quality in the color flow Doppler mode. During conditions in which the anatomy being imaged is the same kidney but the user inputs a request to transition from the color flow Doppler mode to the B-mode, the ultrasound imaging system may provide a second set of recommended imaging parameters (which may be different than the first set of imaging parameters), with the second set of imaging parameters configured to increase the imaging quality in the B-mode. Although the B-mode and color flow Doppler mode are described above as examples, other modes are possible (e.g., M-mode, Color M-mode, spectral Doppler mode, etc.).

The ultrasound imaging system 100 determines the anatomy being imaged via one or more algorithms (e.g., image processing algorithms such as edge detection, machine learning models 119, deep neural network, etc.) stored in memory 120, and uses the determination of the anatomy being imaged with the one or more algorithms to provide recommended imaging parameters to the user. For example, the ultrasound imaging system 100 may identify features of the images acquired during imaging (e.g., during a scan of a patient) associated with various anatomical structures and/or regions of the body, such as bones, blood vessels, organs, etc., based on a shape, relative proximity, apparent depth, orientation, etc. of said features. Based on the features identified, the ultrasound imaging system 100 may determine the anatomical structures being imaged. As one example, during conditions in which the user operates the ultrasound imaging system 100 to image the aorta of a patient, the ultrasound imaging system 100 may determine that the aorta is being imaged based on a movement and/or orientation of the aorta relative to surrounding structures, such as the brachiocephalic artery, via a deep learning classification model trained to recognize the movement and/or orientation of the aorta and other anatomical structures.

In some embodiments, the ultrasound imaging system 100 may perform a verification of the anatomy being imaged immediately following a transition from a first imaging mode to a second imaging mode. For example, responsive to an imaging mode transition request (e.g., a user input indicating that a transition from a first imaging mode, such as the B-mode, to a second imaging mode, such as the color flow Doppler mode, is desired), the ultrasound imaging system 100 may analyze a pre-determined number of images (e.g., five images) stored in memory that were acquired sequentially by the ultrasound imaging system immediately prior to the transition request, as described above, which may be referred to as a first set of images. The ultrasound imaging system may determine the anatomy being imaged (e.g., a kidney) following the transition request and prior to transitioning from the first imaging mode to the second imaging mode, with the determination based on the images acquired prior the transition request according to an algorithm or model (e.g., deep learning model) stored in the memory of the ultrasound imaging system.

After determining the anatomy being imaged, the ultrasound imaging system may transition from the first imaging mode to the second imaging mode. However, after transitioning to the second imaging mode, the ultrasound imaging system 100 may perform the verification (e.g., re-determination) of the anatomy being imaged by acquiring a second set of images (e.g., via probe 106) sequentially while operating in the second imaging mode. The second set of images may include a same number of images as the first set of images in some examples, and in other examples, the second set of images may include a different number of images (e.g., ten images).

The algorithm or model that determines the anatomy being imaged prior to the transition request may additionally analyze image information (e.g., color information) of one or more images of the second set of images acquired after transitioning to the second imaging mode and compare the image information to an expected amount of image information in order to verify that the anatomy imaged while in the first imaging mode is the same anatomy imaged while in the second imaging mode. For example, during conditions in which the second imaging mode is the color flow Doppler mode, the algorithm or model may compare an amount of color information in each image of the second set of images to an expected amount of color information, where the expected amount of color information may be different for different anatomical structures. In some examples, the expected amount of color information may be stored in a look-up table in the memory of the controller (e.g., with an input being the anatomy being imaged, and with an output being the expected amount of color information), and in some examples, the expected amount of color information may be a function of both the anatomy being imaged and an imaging parameter such as the depth of the anatomy, patient age, patient weight, etc. In other examples in which the second imaging mode is different than the color flow Doppler mode (e.g., the M-mode), the algorithm or model may verify the anatomy being imaged while in the second imaging mode in a different way, such as comparing elasticity information of the anatomy in each image of the second set of images to an expected elasticity, where the expected elasticity may be different for different anatomical structures. Other examples are possible.

Following the determination of the anatomy being imaged based on the first set of images, the ultrasound imaging system 100 stores the determined anatomy in memory. After verifying the anatomy imaged in the second imaging mode as described above, the ultrasound imaging system 100 may compare the results of the verification (e.g., the anatomy determined based on the second set of images) with the anatomy determined while imaging in the first imaging mode (e.g., the anatomy determined prior to the transition to the second imaging mode and responsive to the transition request, based on the first set of images). If the anatomy has not changed (e.g., the anatomy stored in memory and determined via the first set of images matches the anatomy determined via the second set of images), the ultrasound imaging system 100 may maintain the anatomy stored in memory (e.g., not change the anatomy stored in memory). However, if the anatomy has changed (e.g., the anatomy stored in memory does not match the anatomy determined via the second set of images), the ultrasound imaging system 100 may update the anatomy stored in memory to the anatomy determined via the second set of images and may update the recommended imaging parameters generated by the ultrasound imaging system 100 using the updated anatomy. In still further examples, if the anatomy determined from the second set of images does not match the anatomy determined in the first set of images (of the anatomy in the second set of images cannot be ascertained) and the system has a high confidence that the ultrasound probe has not moved significantly (e.g., based on feedback from probe motion sensors, an in-room camera, or other probe motion tracking mechanism), the mismatching or non-identified anatomy in the second set of images may be attributed to the recommended imaging parameters (e.g., recommended based on the first set of images) generating low quality images. In such an example, the system may recommend different imaging parameters or may request the operator update the imaging parameters.

In some examples, the one or more algorithms (e.g., deep neural network) used by the ultrasound imaging system 100 to provide the recommended imaging parameters responsive to an imaging mode transition request may analyze previous inputs by users of the ultrasound imaging system 100 to provide more accurate recommended parameters. For example, during conditions in which a user operating the ultrasound imaging system 100 inputs an imaging mode transition request, the ultrasound imaging system 100 provides recommended imaging parameters based on the anatomy being imaged, as described above. If the user rejects the recommended imaging parameters (e.g., selects imaging parameters other than the recommended imaging parameters), the ultrasound imaging system 100 may adjust future recommended imaging parameters based on the imaging parameters selected by the user. As one example, the one or more algorithms of the ultrasound imaging system 100 may recognize that during imaging of a kidney, the user frequently rejects the recommended imaging parameters provided by the ultrasound imaging system 100 and instead inputs custom imaging parameters. As a result, the ultrasound imaging system 100 may adjust the recommended imaging parameters to be closer in value to the imaging parameters input by the user over a number of transition requests. However, in other examples, the recommended imaging parameters for different anatomical structures may be pre-determined (e.g., stored in a data table), and the ultrasound imaging system 100 may provide the same recommended imaging parameters for a given anatomy being imaged regardless of previous user inputs.

As described above, the recommended imaging parameters provided by the ultrasound imaging system 100 are based on the determined anatomy being imaged. In some examples, the anatomy being imaged, as determined by the ultrasound imaging system 100, may be a less localized region of the body, such as the abdomen. In other examples, the anatomy being imaged may be a structure more localized within the region, such as an appendix within the abdomen. As such, the anatomy being imaged, as determined by the ultrasound imaging system 100, may include both of the less localized region, such as the abdomen, and the more localized structure, such as the appendix. When the user requests a transition between imaging modes, the ultrasound imaging system 100 may base the recommended imaging parameters on the more localized structure if the ultrasound imaging system 100 has determined that the structure is being imaged (e.g., based on the images acquired sequentially immediately prior to the transition request, as described above). However, during conditions in which the ultrasound imaging system 100 is unable to determine the more localized structure being imaged (e.g., due to increased noise, movement, etc.), the ultrasound imaging system 100 may instead provide recommended imaging parameters based on the less localized region being imaged (e.g., the abdomen).

Further, in some examples, probe 106 of ultrasound imaging system 100 may include a position sensor configured to sense a location of the probe 106 relative to one of more reference locations. For example, the position sensor of probe 106 may continuously track a movement of the probe 106 (e.g., rotation, translation, orientation, etc. of the probe 106) relative to the location of the probe 106 at the time the determination of the anatomy being imaged is made. The position sensor may transmit the location information to the ultrasound imaging system 100, and responsive to an imaging mode transition request, the ultrasound imaging system 100 may utilize the location information in combination with the analysis of the pre-determined number of images acquired sequentially immediately prior to the transition request (as described above) in order to increase an accuracy of the determination of the anatomy being imaged.

In some examples, during conditions in which the position of the probe 106 is tracked via the position sensor and the probe 106 has not been moved between separate imaging mode transition requests, the ultrasound imaging system 106 may determine that the same anatomy is being imaged at each transition request. For example, responsive to a first imaging mode transition request at time t1 (e.g., transitioning from B-mode to color flow Doppler mode), the ultrasound imaging system 100 determines the anatomy being imaged based on the pre-determined number of images acquired sequentially immediately prior to the first transition request, as described above. During the request, the probe 106 may be maintained at a given location. After some time elapses (e.g., 10 seconds, 20 seconds, etc.), without moving the probe 106 from the given location, the operator may input a second imaging mode transition request at time t2 (e.g., to transition back to B-mode from color flow Doppler mode). Because the probe 106 has not been moved following the first transition request (e.g., not moved between time t1 and time t2), the ultrasound imaging system 100 may determine, responsive to the second imaging mode transition request, that the anatomy being imaged at time t2 is the same anatomy imaged at time t1.

In some examples, the ultrasound imaging system 100 may additionally analyze an amount of image information of one or more images acquired after transitioning to the second imaging mode and compare the amount of image information to an expected amount of image information in order to update the recommended imaging parameters. For example, the ultrasound imaging system 100 may acquire a second set of sequential images following the transition to the second imaging mode (e.g., similar to the second set of images described above), and during conditions in which the second imaging mode is the color flow Doppler mode, the ultrasound imaging system 100 may compare an amount of color information in each image of the second set of images to an expected amount of color information, where the expected amount of color information may be different for different anatomical structures (similar to the examples described above). For example, the expected amount of color information may be a function of both the anatomy being imaged and the imaging parameters used to acquire the second set of images in the second imaging mode. If the amount of color information is different than the expected amount of color information, the ultrasound imaging system 100 may update the recommended imaging parameters based on the difference between the acquired amount of color information and the expected amount of color information. As one example, the ultrasound imaging system 100 may modify (e.g., update) a given parameter (e.g., pulse repetition frequency) of the recommended imaging parameters via a function stored in memory, with the difference between the acquired amount of color information and the expected amount of color information as one input and the unmodified recommended pulse repetition frequency as a second input, and with an updated recommended pulse repetition frequency as an output. Other examples are possible. In still further examples, the intensity and/or distribution of the color information in the acquired color flow images may provide a validation check on whether the correct anatomy was identified. For example, when imaging the kidney in the color flow Doppler mode, the color information may be distributed across the kidney with the inflow/outflow colors somewhat evenly distributed/present (see FIG. 8, for example). In contrast, when imaging the aorta in color flow Doppler mode, the color information may be less uniformly distributed, and may include concentrated areas of inflow and concentrated areas of outflow (see FIG. 5, for example). If the color information is not distributed as expected, the method may determine that the original anatomy identification was incorrect and re-identify the anatomy (e.g., using the second set of images) and/or ask the operator to confirm the imaged anatomy, upon which the imaging parameters may be adjusted (e.g., if the anatomy was incorrect and thus the wrong imaging parameters were applied).

Figure 2:
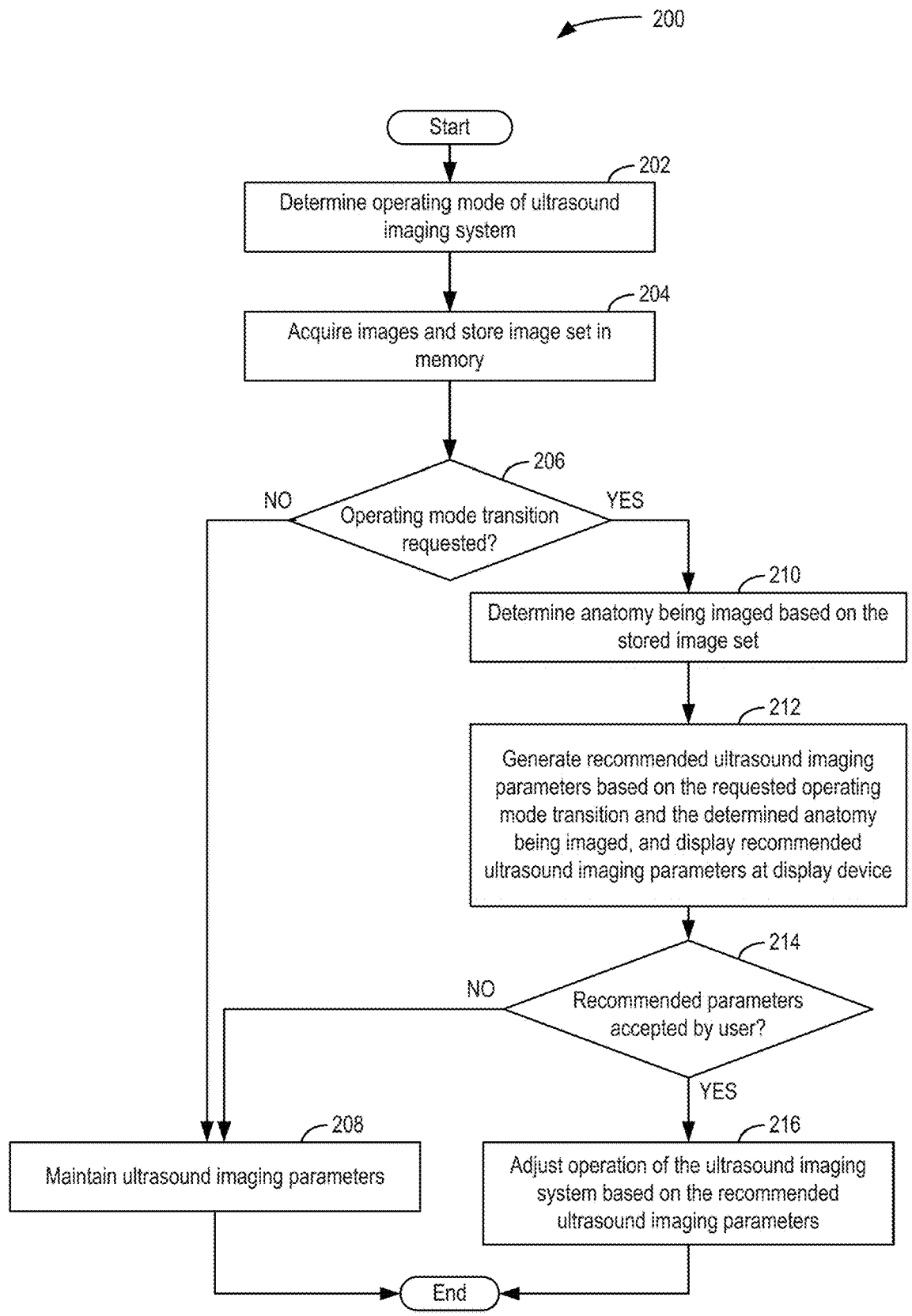
FIG. 2 shows a flow chart illustrating a method for controlling ultrasound imaging parameters based on user input.

Referring now to FIG. 2, a flowchart is shown illustrating a method 200 for controlling operation of an ultrasound imaging system. In at least one example, the ultrasound imaging system referred to by method 200 is the ultrasound imaging system 100 described above with reference to FIG. 1, and method 200 may be implemented by the ultrasound imaging system 100. In some embodiments, method 200 may be implemented as executable instructions in a memory of the ultrasound imaging system, such as the memory 120 of FIG. 1.

At 202, an operating mode of the ultrasound imaging system is determined. The operating mode may include an imaging mode of a probe (e.g., probe 106 shown by FIG. 1 and described above) of the ultrasound imaging system. The operating mode may include any of the imaging modes described above, such as the B-mode, color flow Doppler mode, M-mode, Color M-mode, spectral Doppler, Elastography, TVI, strain, strain rate, and the like. For each operating mode, the ultrasound imaging system may control the probe in a different way (e.g., control signals transmitted to the transducers of the probe, or process signals received from the transducers of the probe, in different ways). Determining the operating mode may include determining an imaging mode selected by a user of the ultrasound imaging system (e.g., an operator, such as a clinician) via a user input device (e.g., a button or other physical control of the probe, an input to a GUI displayed at a touch screen display device, etc.). The user input device may be the user interface 115 referenced above with regard to FIG. 1, in some examples. The selected imaging mode may be stored in the memory of the ultrasound imaging system, and the determination of the operating mode may include retrieving the selected imaging mode from the memory.

At 204, one or more ultrasound images and/or cine loops are acquired (e.g., via the ultrasound probe) and an image set is stored in memory. The memory may be the memory of the ultrasound imaging system, such as the memory 120 described above with reference to FIG. 1. The image set may include a pre-determined number of images and/or cine loops (e.g., five images, ten images, twenty images, etc.) acquired sequentially by the ultrasound imaging system. In some examples, the image set may be continuously updated by the ultrasound imaging system as new images are acquired. For example, the image set may comprise five images acquired sequentially by the ultrasound imaging system. Acquisition of a sixth image may result in removal of the oldest image from the image set, such that the images stored within the image set are the most recently acquired images in sequential order (e.g., order of acquisition).

At 206, a determination is made of whether an operating mode transition is requested. An operating mode transition includes an input by the user of the ultrasound imaging system to adjust from a first imaging mode (e.g., B-mode) to a different, second imaging mode (e.g., color flow Doppler mode). As described above, the operating mode may be selected by the user via the user input device, which may comprise a button or other physical control of the probe, an input to a GUI displayed at a touch screen display device, and the like. The user input device may be the user interface 115 referenced above with regard to FIG. 1. As one example, the user may operate the ultrasound imaging system in the first imaging mode and may press a button on the probe (e.g., probe 106 shown by FIG. 1) in order to input the transition request to operate the ultrasound imaging system in the second mode. As another example, the user may operate the ultrasound imaging system in the first imaging mode and may input a mode transition at a GUI of a display device of the ultrasound imaging system (e.g., via a mouse, keyboard, trackball, etc., or via touch for configurations in which the display device includes a touch screen) in order to transition (e.g., adjust) the ultrasound imaging system to operate in the second imaging mode.

If an operating mode transition is not requested at 206, ultrasound imaging parameters are maintained at 208. Maintaining the parameters may include not transitioning the imaging mode of the ultrasound imaging system (e.g., maintaining the ultrasound imaging system in the first imaging mode, and not transitioning the ultrasound imaging system to the second imaging mode).

However, if an operating mode transition is requested at 206, an anatomy and/or scan plane being imaged is determined based on the stored image set at 210. For example, the user of the ultrasound imaging system may input a selection to transition operation of the ultrasound imaging system from the first mode to the second mode at 206. As a result, at 210, the ultrasound imaging system analyzes the image set stored in memory in order to determine the anatomy being imaged. The determination of the anatomy being imaged may be similar to the example described above with reference to FIG. 1. For example, the ultrasound imaging system may utilize one or more algorithms (e.g., machine learning models, deep neural networks, etc.) to analyze the image set and determine the anatomy being imaged, where analysis of the image set may include determining various anatomical structures and/or regions of the body shown by the images, such as bones, blood vessels, organs, etc. based on a shape, relative proximity, apparent depth, orientation, etc., of said features. Further, the view or scan plane being imaged may be identified. For example, the system may determine that a heart is being imaged, and then further identify that a four-chamber view of the heart is currently being imaged (e.g., as opposed to a two-chamber view, three-chamber view, etc.). By analyzing the set of images rather than a single image, the confidence in the detected anatomy may be increased. Further, motion of one or more structures in the images may be detected by comparing the location, shape, size, etc., of identified structures across the set of images, which may assist in identifying certain anatomical features. Further still, when switching from the first operating mode to the second operating mode, a first number of images may be analyzed (e.g., five) while a different number of images may be analyzed when switching from the second operating mode to the first operating mode (e.g., ten images). For example, when operating in color flow Doppler mode, the image quality of the underlying anatomical features may not be as high as when imaging in B-mode, and thus more images may be analyzed when switching from color flow Doppler mode than when switching from B-mode in order to increase the confidence in the anatomy detection.

At 212, recommended ultrasound imaging parameters are generated based on the requested operating mode transition and the determined anatomy and/or scan plane being imaged, and the recommended ultrasound imaging parameters are displayed at a display device. Similar to the examples described above with reference to ultrasound imaging system 100 shown by FIG. 1, the recommended ultrasound imaging parameters may be different for different operating modes and different anatomies and/or scan planes. For example, during conditions in which the anatomy being imaged is a kidney (as one non-limiting example) and the user inputs a request to transition from the B-mode to the color flow Doppler mode, a first set of recommended imaging parameters may be generated, with the first set of recommended imaging parameters configured to increase the imaging quality in the color flow Doppler mode. During conditions in which the anatomy being imaged is the same kidney but the user inputs a request to transition from the color flow Doppler mode to the B-mode, the ultrasound imaging system may provide a second set of recommended imaging parameters (which may be different than the first set of imaging parameters), with the second set of imaging parameters configured to increase the imaging quality in the B-mode. Images acquired by the ultrasound imaging system in the color flow Doppler mode may include grayscale information (e.g., monochromatic image data) as well as color information (e.g., color flow image data colored according to a color reference, such as color reference 703 shown by FIG. 7 and described below).

In some examples, while switching from the color flow Doppler mode to the B-mode, the ultrasound imaging system may analyze only the grayscale information or only the color flow information of the images acquired while operating in the color flow Doppler mode to generate the recommended imaging parameters for the B-mode. Further, when transitioning between other modes, such as transitioning from Elastography mode to TVI mode, the ultrasound imaging system may analyze only a portion of image information acquired in the operating mode prior to the transition (e.g., the Elastography mode) in order to generate the recommended imaging parameters for the transitioned mode (e.g., the TVI mode).

In some examples, while determining the anatomy being imaged responsive to a transition request to transition from the color flow Doppler mode to the B-mode, the ultrasound imaging system may analyze only the grayscale information portion or only the color flow information of the images acquired in the color flow Doppler mode to determine the anatomy imaged. Similarly, while transitioning between other modes, such as transitioning from Elastography mode to TVI mode, the ultrasound imaging system may analyze only a portion of image information acquired in the operating mode prior to the transition (e.g., the Elastography mode) in order to determine the anatomy being imaged. Analyzing only the portion of the image information may reduce a load (e.g., processing load and/or analysis time) of the ultrasound imaging system.

In still further examples, the anatomy determination described above may only function as intended on images acquired in certain modes, such as B-mode images. When transitioning from an imaging mode where image information is not suitable for anatomy detection (e.g., M-mode), the method may include transiently operating in an imaging mode where suitable images may be acquired for anatomy detection, such as transiently operating in B-mode to acquire a set of images that may then be entered into the model to determine the anatomy being imaged. Once the images have been acquired for anatomy detection, the mode switch to the requested operating mode may be initiated. In some examples, before entering the images into the model to detect the anatomy, the B-mode images may be displayed and the operator may be requested to confirm that the imaged view/scan plane is the desired view/scan plane.

The recommended imaging parameters may be displayed at the display device, such as the display device 118 of FIG. 1. The user may interact with the display device via the user interface (e.g., user interface 115 of FIG. 1) in order to confirm or reject the recommended imaging parameters. Examples of recommended imaging parameters based on the requested mode transition and anatomy being imaged that may be displayed at the display device are shown by FIGS. 5 and 8 and described further below.

The recommended imaging parameters may be stored in memory of the ultrasound system in a look-up table or other data structure indexed by anatomy and requested imaging mode. In other examples, the recommended imaging parameters may be determined by a model that uses the identified anatomy as an input to determine the recommended imaging parameters. The model may further use prior user imaging parameters as inputs, which may allow the model to be tailored to a particular user's preferred imaging parameters. In some examples, the model may use the imaging parameters used to acquire the set of images in the first operating mode as an input, along with the identified anatomy, to determine the recommended imaging parameters. For example, the imaging parameters used to acquire B-mode images (e.g., depth, frequency) may provide an indication of certain patient-specific features, such as patient thickness, that may impact image quality but may not be apparent from the B-mode images/identified anatomy themselves. By accounting for the imaging parameters used to acquire the images in the first operating mode, the recommended imaging parameters for the second operating mode may be fine-tuned based on the specific patient, for example.

In some examples, the images themselves may be input into a model that determines the recommended imaging parameters. The model may selected from among a plurality of models based on the anatomy being imaged, the current imaging mode, and the requested imaging mode. For example, a first model may be selected when a kidney is imaged in B-mode and the user requests to image in a color flow Doppler mode, and a second model may be selected when an aorta is being imaged in B-mode and the user requests to image in color flow Doppler mode; a third model may be selected when the kidney is imaged in color flow Doppler mode and the user requests to image in B-mode. Each model may be a machine learning model (e.g., a convolutional neural network) that is trained using images acquired in the first mode and recommended imaging parameters and image quality for the second mode as ground truth labels. For example, the training data used to train a first, kidney-specific model may include a plurality of data sets, with each data set including a first image of the kidney acquired in a first mode (e.g., B mode) and a second image of the kidney acquired immediately after acquisition of the first image, but in a second mode (e.g., color flow Doppler mode). The imaging parameters used to acquire the second image may be included as ground truth labels for the first image, along with an expert (e.g., physician) annotation indicating a relative image quality of the second image.

At 214, a determination is made of whether the recommended ultrasound imaging parameters are accepted by the user. For example, displaying the recommended imaging parameters at 212 may include displaying buttons at the GUI of the ultrasound imaging system, with a first button configured to confirm (e.g., accept) the recommended ultrasound imaging parameters, and with a second button configured to reject (e.g., discard) the recommended ultrasound imaging parameters. Determining whether the recommended ultrasound imaging parameters are accepted by the user may include determining whether the user has input commands via the user interface device to accept the recommended ultrasound imaging parameters (e.g., select the first button) or reject the recommended ultrasound imaging parameters (e.g., select the second button).

If the user does not accept the recommended ultrasound imaging parameters at 214, the ultrasound imaging parameters are maintained at 208. For example, maintaining the parameters may include not adjusting the ultrasound imaging parameters based on the recommended ultrasound imaging parameters (e.g., maintaining ultrasound imaging parameters utilized prior to the operation mode transition request). In some examples, in response to the user rejecting the recommended ultrasound imaging parameters, a menu or other graphical user interface feature may be displayed, via which the user may select/adjust any desired ultrasound imaging parameters. In some examples, in response to the user rejecting the recommended ultrasound imaging parameters, default ultrasound imaging parameters for the imaging mode may be utilized.

However, if the user does accept the recommended ultrasound imaging parameters at 214, operation of the ultrasound imaging system is adjusted based on the recommended ultrasound imaging parameters at 216. For example, prior to the operating mode transition request, the probe of the ultrasound imaging system may be operating in the B-mode with a first (e.g., default) pulse repetition frequency (PRF), such as 2.5 pulses per second. Responsive to an operating mode transition request to transition to imaging in the color flow Doppler mode, the ultrasound imaging system determines the anatomy being imaged (as described above) and generates a recommended PRF based on imaging the anatomy in the color flow Doppler mode. As one non-limiting example, the recommended PRF may be 2.1 pulses per second. Responsive to the determination that the user has accepted the recommended ultrasound imaging parameters, the first PRF value is replaced with the recommended PRF value such that the operation of the probe is adjusted from the first PRF to the recommended PRF (e.g., adjusted from 2.5 pulses per second to 2.1 pulses per second). Although the PRF is described herein as an example parameter, the recommended ultrasound imaging parameters may include one or more other parameters (e.g., packet size, wall filter setting, spatial filter setting, etc.). Adjusting operation of the ultrasound imaging system using the recommended imaging parameters may increase a clarity of images generated by the ultrasound imaging system. Non-limiting example images and parameters are described below with reference to FIGS. 3-8.

Referring now collectively to FIGS. 3-5, different ultrasound images of a first anatomical structure acquired via an ultrasound imaging system are shown. The ultrasound images shown by FIGS. 3-5 may be acquired by the ultrasound imaging system 100 shown by FIG. 1 and described above. The first anatomical structure shown by the ultrasound images of FIGS. 3-5 is an aorta of a patient. The ultrasound images shown by FIGS. 3-5 may be displayed at a display device of the ultrasound imaging system, such as display device 118 of ultrasound imaging system 100 shown by FIG. 1 and described above.

FIG. 3 shows ultrasound image 300 of aorta 302 of the patient, with the ultrasound image 300 acquired by the ultrasound imaging system while operating in the B-mode. Ultrasound image 300 may be representative of images acquired by the ultrasound imaging system prior to an imaging mode transition request, where the imaging mode transition request is similar to the transition requests described above. For example, ultrasound image 300 may be one image of a group of images acquired sequentially by the ultrasound imaging system while imaging in the B-mode, prior to transitioning the ultrasound imaging system to imaging in the color flow Doppler mode. The imaging mode transition request may include receiving an input from an operator of the ultrasound imaging system (e.g., a clinician) at a user input device (e.g., user interface 115 shown by FIG. 1 and described above) indicating that a transition from imaging in the B-mode to imaging in the color flow Doppler mode is desired. Although not shown by FIG. 3, image 300 may be displayed by the display device along with imaging parameters and/or other imaging data (e.g., patient information). Further, in some examples, the operator of the ultrasound imaging system may update or change the imaging parameters by inputting the updated parameters to the ultrasound imaging system via the user interface. As one example, changing a pulse repetition frequency (PRF) value of the ultrasound imaging system may include selecting a PRF field of a GUI displayed at the display device via one or more input devices (e.g., mouse, keyboard, touch screen, etc.) and inputting the updated PRF value via the one or more input devices. Example GUI features are described below with reference to FIGS. 4-5.

Referring to FIG. 4, ultrasound image 400 of aorta 302 of the patient is shown, with the ultrasound image 400 acquired by the ultrasound imaging system while operating in the color flow Doppler mode. In particular, ultrasound image 400 is acquired by the ultrasound imaging system without using recommended imaging parameters generated by the ultrasound imaging system (as described above with reference to FIGS. 1-2). For example, ultrasound image 400 may be acquired by the ultrasound imaging system during conditions in which the operator rejects the recommended imaging parameters generated by the ultrasound imaging system following an imaging mode transition request (e.g., a request input by the operator to transition from the B-mode to the color flow Doppler mode). FIG. 4 additionally shows GUI 402 including a list of imaging parameters 404 and color reference 403. Imaging parameters 404 are the imaging parameters of the ultrasound imaging system during acquisition of the image 400. Imaging parameters 404 may be default imaging parameters (e.g., unadjusted imaging parameters) associated with the color flow Doppler mode. Imaging parameters 404 are not adjusted by the ultrasound imaging system based on the anatomy being imaged (e.g., the aorta 302). Color reference 403 may be used in combination with color flow mapping 405 by the operator or other clinician (e.g., a cardiologist) in order to determine the direction and/or speed of blood flowing within the anatomy being imaged.

The clarity of the color flow mapping 405 (e.g., a resolution or amount of color gradation of the color flow mapping 405) may result from the values of the imaging parameters 404. Although the ultrasound imaging system may utilize default imaging parameter values during conditions in which the operator rejects the recommended imaging parameter values, the default imaging parameter values may not provide increased clarity of the color flow mapping 405 for various anatomical structures. For example, while imaging a first anatomical structure (e.g., aorta 302) using the default imaging parameter values, the clarity of the color flow mapping may be different relative to conditions in which a second anatomical structure (e.g., a kidney) is imaged using the default imaging parameter values. Further, in some examples, the default imaging parameter values may not provide sufficient image clarity for a wide variety of anatomical features (e.g., it may be difficult for the operator to observe the anatomy being imaged or diagnose the patient due to poor image clarity resulting from the default imaging parameter values). Although the operator may manually input different imaging parameter values in order to attempt to increase the image clarity, the approach of manually inputting values may increase a cognitive load on the operator and increase imaging time. Further, inputting values manually may include a trial-and-error approach in which the operator attempts a variety of different imaging parameter values due to uncertainty as to whether particular imaging parameter values should be increased, decreased, or maintained, which may additionally increase imaging time and operator cognitive load.

However, the ultrasound imaging system is configured to generate recommended imaging parameter values responsive to an imaging mode transition request, similar to the examples described above. By accepting the recommended imaging parameter values, the clarity of images generated by the ultrasound imaging system may be increased, resulting in decreased imaging time, reduced cognitive load of the operator, and/or increased accuracy of patient diagnosis. As an example of an image having increased clarity as a result of the recommended imaging parameters generated by the ultrasound imaging system, FIG. 5 shows ultrasound image 500 of aorta 302. Ultrasound image 500 is provided for relative comparison with the ultrasound image 400 shown by FIG. 4. As shown by FIG. 5, GUI 402 includes updated imaging parameters 504, with unadjusted (e.g., default) imaging parameter values shown in strikethrough text, and with the recommended (e.g., adjusted) imaging parameter values generated by the ultrasound imaging system shown in bold text. The ultrasound image 500 is generated by the ultrasound imaging system using the recommended imaging parameter values. As a result, the clarity (e.g., resolution and/or amount of color gradation) of color flow mapping 505 is increased relative to the color flow mapping 405 of ultrasound image 400 shown by FIG. 4. As shown in FIG. 5, the recommended imaging parameters may include a PRF of 2.3 (instead of the PRF of 2.6 of the default parameters), a wall filter of 263 (instead of a wall filter of 191 for the default parameters), a spatial filter of 5 (instead of a spatial filter of 3 for the default parameters), and a packet size of 8 (instead of a packet size of 12 for the default parameters).

Further, as described above, the ultrasound imaging system determines the anatomy being imaged based on images acquired prior to transitioning to the color flow Doppler imaging mode (e.g., based on images acquired while imaging in the B-mode immediately prior to transitioning to imaging in the color flow Doppler mode). The GUI 402 may display a name of the anatomy being imaged via an anatomy identification field 506, in some examples. Further, the GUI 402 may display a notification area 508 including a confirm button 510 and a reject button 512. The operator may input a selection to the notification area 508 in order to accept the recommended imaging parameter values (e.g., replace default imaging parameter values with the recommended imaging parameter values by selecting the confirm button 510) or reject the recommended imaging parameter values (e.g., by selecting the reject button 512, to revert to the default imaging parameter values for example).

Now referring to FIG. 6, an ultrasound image 600 is shown. Ultrasound image 600 is acquired while imaging a patient with the same ultrasound imaging system described above with reference to FIGS. 3-5 in the B-mode. However, while ultrasound image 300 shown by FIG. 3 shows the aorta 302 of the patient, ultrasound image 600 shown by FIG. 6 shows a kidney 602 of the patient. Ultrasound image 600 may be one of a plurality of ultrasound images acquired sequentially by the ultrasound imaging system while operating in the B-mode.

FIG. 7 shows an ultrasound image 700 of the kidney 602 of the patient, with the ultrasound image 700 acquired while operating the ultrasound imaging system in the color flow Doppler imaging mode with imaging parameters 704. Imaging parameters 704 may be default (e.g., unadjusted) imaging parameters of the ultrasound imaging system. For example, responsive to transitioning the ultrasound imaging mode from imaging in the B-mode to imaging in the color flow Doppler mode, the ultrasound imaging system generated recommended imaging parameters for the color flow Doppler mode based on the anatomy being imaged (e.g., the kidney 602), with the anatomy being imaged determined based on images acquired while operating in the B-mode (e.g., similar to the examples described above). The ultrasound image 700 shown by FIG. 7 is an image acquired without using the recommended imaging parameters. As one example, the operator may reject the recommended imaging parameters and may continue imaging using default imaging parameters (e.g., imaging parameters 704), which may result in a reduced clarity of ultrasound image 700 (e.g., a reduced resolution and/or amount of color gradation of color flow mapping 705). In some examples, the imaging parameters 704 may be the same as the imaging parameters 404 shown by FIG. 4.

GUI 702 includes color reference 703, similar to the color reference 403 shown by FIG. 4 and described above. Color reference 703 may be used in combination with color flow mapping 705 by the operator or other clinician (e.g., a cardiologist) in order to determine the direction and/or speed of blood flowing within the anatomy being imaged (e.g., the kidney 602).

Referring now to FIG. 8, an ultrasound image 800 is shown. Ultrasound image 800 is acquired by the ultrasound imaging system using the recommended imaging parameters generated by the ultrasound imaging system based on the anatomy being imaged (e.g., the kidney 602) and responsive to the imaging mode transition request (e.g., the input by the operator indicating that transitioning the ultrasound imaging system from imaging in the B-mode to imaging in the color flow Doppler mode is desired). The ultrasound image 800 has an increased image clarity relative to ultrasound image 700 acquired without using the recommended imaging parameters.

As shown by FIG. 8, GUI 702 includes updated imaging parameters 804, with unadjusted (e.g., default) imaging parameter values shown in strikethrough text, and with the recommended (e.g., adjusted or updated) imaging parameter values generated by the ultrasound imaging system shown in bold text. Similar to the example described above with reference to FIG. 5, the GUI 702 may display a name of the anatomy being imaged (e.g., the kidney) via an anatomy identification field 806. Further, the GUI 702 may display a notification area 808 including a confirm button 810 and a reject button 812, similar to notification area 506, confirm button 510, and reject button 512 of FIG. 5, respectively.

The recommended imaging parameters (e.g., recommended imaging parameter values) generated by the ultrasound imaging system as shown by FIG. 8 are based on the anatomy being imaged (e.g., the kidney). As a result, the recommended imaging parameters shown by FIG. 8 differ from the recommended imaging parameters shown by FIG. 5, due to the recommended imaging parameters shown by FIG. 5 being based on imaging a different anatomical structure (e.g., the aorta). For example, the recommended parameters for the kidney may include a PRF of 1, a wall filter of 108, a spatial filter of 3, and a packet size of 12. During conditions in which a different, third anatomical structure is imaged (e.g., different from the aorta and kidney), the ultrasound imaging system provides recommended imaging parameter values based on the third anatomical structure, which may be different from the recommended imaging parameters shown by FIGS. 5 and 8. In this way, the recommended imaging parameters provided by the ultrasound imaging system may increase the clarity of images acquired by the ultrasound imaging system for a wide variety of different anatomical structures.

The technical effect of generating the recommended imaging parameters based on the anatomy being imaged is to increase the clarity of images acquired by the ultrasound imaging system while reducing a cognitive load on an operator of the ultrasound system.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
operating an ultrasound imaging system in a first operating mode;
acquiring a plurality of sequential ultrasound images of an anatomy while operating the ultrasound imaging system in the first operating mode prior to receiving an operating mode transition request;
receiving the operating mode transition request;
determining the anatomy imaged by the ultrasound imaging system in the first operating mode by analyzing the plurality of sequential ultrasound images via a machine learning model stored in a memory of the ultrasound imaging system;
generating recommended imaging parameters for a second operating mode based on the anatomy imaged in the first operating mode, wherein a type of image information obtained in the first operating mode is different than a type of image information obtained in the second operating mode, wherein the recommended imaging parameters that are generated is a set of recommended imaging parameters during a condition in which the first operating mode comprises B-mode and the second operating mode comprises color flow Doppler mode, and wherein the set of recommended imaging parameters is configured to increase imaging quality in the color flow Doppler mode; and adjusting imaging parameters of the ultrasound imaging system in the second operating mode based on the first operating mode and the anatomy imaged in the first operating mode, wherein a same portion of the anatomy is imaged in the first and second operating mode.

2. The method of claim 1, further comprising, responsive to the operating mode transition request and while operating in the second operating mode, determining the anatomy imaged by the ultrasound imaging system in the second operating mode based on images acquired by the ultrasound imaging system in the second operating mode, and further adjusting the imaging parameters.

3. The method of claim 1, wherein the operating mode transition request includes selection of the second operating mode via a user interface device of the ultrasound imaging system.

4. The method of claim 1, wherein generating recommended imaging parameters for the second operating mode based on the anatomy imaged in the first operating mode further comprises acquiring at least one image in the second operating mode, comparing a determined amount of image information of the at least one image to an expected amount of image information, and updating the recommended imaging parameters based on a difference between the determined amount of image information and the expected amount of image information, wherein the expected amount of image information is different for different anatomical structures.

5. The method of claim 1, further comprising displaying the recommended imaging parameters at a display device of the ultrasound imaging system.

6. The method of claim 5, wherein adjusting imaging parameters of the ultrasound imaging system in the second operating mode includes replacing default imaging parameters with the recommended imaging parameters.

7. The method of claim 1, wherein determining the anatomy imaged by the ultrasound imaging system in the first operating mode includes determining a position of a probe of the ultrasound imaging system via a probe position sensor while operating the ultrasound imaging system in the first operating mode.

8. The method of claim 1, wherein the recommended imaging parameters that are generated is a first set of recommended imaging parameters during a first condition in which the first operating mode comprises B-mode and the second operating mode comprises color flow Doppler mode, and wherein the recommended imaging parameters that are generated is a second set of recommended imaging parameters during a second condition in which the first operating mode comprises the color flow Doppler mode and the second operating mode comprises the B-mode, wherein the first set of recommended imaging parameters is configured to increase imaging quality in the color flow Doppler mode, and wherein the second set of recommended imaging parameters is configured to increase imaging quality in the B-mode.

9. An ultrasound imaging system, comprising:
an ultrasound probe; and
a controller with computer readable instructions stored on non-transitory memory that when executed, cause the controller to:
responsive to a request to transition from a first operating mode to a second operating mode while in the first operating mode, acquire a plurality of images of an anatomy with the ultrasound probe while in the first operating mode;
determine the anatomy currently being imaged by the ultrasound imaging system based on one or more of the plurality of images by analyzing the plurality of sequential ultrasound images via a machine learning model stored in a memory of the ultrasound imaging system; and then
acquire, with the ultrasound probe, one or more images in the second operating mode, the one or more images acquired in the second operating mode acquired with imaging parameters of the ultrasound imaging system selected based on the determined anatomy, wherein a same portion of the anatomy is imaged in the first and second operating mode,
wherein a type of image information obtained in the first operating mode is different than a type of image information obtained in the second operating mode;
wherein the imaging parameters of the ultrasound imaging system selected based on the determined anatomy are identified automatically by the ultrasound imaging system and are selected to acquire the one or more images in the second operating mode in response to a user input accepting the imaging parameters;
wherein the imaging parameters that are generated is a set of imaging parameters during a condition in which the first operating mode comprises B-mode and the second operating mode comprises color flow Doppler mode, and wherein the set of imaging parameters is configured to increase imaging quality in the color flow Doppler mode.

10. The ultrasound imaging system of claim 9, wherein the imaging parameters of the ultrasound imaging system selected based on the determined anatomy are selected automatically by the ultrasound imaging system.

11. A method, comprising:
acquiring, via an ultrasound probe of an ultrasound imaging system operating in a first mode, one or more first mode images;
determining that a user has requested to operate the ultrasound imaging system in a second mode;
responsive to the request, automatically adjusting one or more imaging parameters of the ultrasound imaging system for the second mode based on an identified scan plane of the one or more first mode images; and
acquiring, via the ultrasound probe of the ultrasound imaging system operating in the second mode, one or more second mode images with the one or more adjusted imaging parameters, wherein a same portion of anatomy is imaged in the first and second mode, and wherein a type of image information obtained in the first mode is different than a type of image information obtained in the second mode, wherein the imaging parameters that are generated is a set of imaging parameters during a condition in which the first mode comprises B-mode and the second mode comprises color flow Doppler mode, and wherein the set of imaging parameters is configured to increase imaging quality in the color flow Doppler mode.

12. The method of claim 11, wherein the one or more imaging parameters of the ultrasound imaging system for the second mode are automatically adjusted based on only a portion of the image information obtained in the one or more first mode images.

13. The method of claim 11, wherein automatically adjusting one or more imaging parameters of the ultrasound imaging system based on the one or more first mode images comprises automatically adjusting the one or more imaging parameters of the ultrasound imaging system based on an anatomical feature identified in the one or more first mode images.

14. The method of claim 1, wherein the plurality of sequential ultrasound images of the anatomy are acquired while operating the ultrasound imaging system in a transient third mode.

15. The method of claim 1, wherein the imaging system does not periodically track the anatomy being imaged.

16. The method of claim 1, wherein the plurality of sequential ultrasound images are acquired immediately prior to the operating mode transition request.

17. The method of claim 1, wherein the recommended imaging parameters that are generated is a first set of recommended imaging parameters during a first condition in which the first operating mode comprises a first type of imaging and the second operating mode comprises a second type of imaging, and wherein the recommended imaging parameters that are generated is a second set of recommended imaging parameters during a second condition in which the first operating mode comprises the second type of imaging and the first operating mode comprises the first type of imaging, the first set of recommended imaging parameters differing from the second set of imaging parameters.

18. The ultrasound imaging system of claim 9, wherein an initial set of imaging parameters is used to acquire the plurality of images with the ultrasound probe while in the first operating mode, and wherein both the initial set of imaging parameters and the determined anatomy are used as inputs to select the imaging parameters used for the one or more images acquired in the second operating mode.

* * * * *